US008822717B2

(12) United States Patent
Salisbury et al.

(10) Patent No.: US 8,822,717 B2
(45) Date of Patent: Sep. 2, 2014

(54) VINYL ACETATE PRODUCTION PROCESS

(75) Inventors: Brian A. Salisbury, Oxford, PA (US); Noel C. Hallinan, Loveland, OH (US); Jenny M. Oran Osment, Cochranville, PA (US)

(73) Assignee: LyondellBassell Acetyls, LLC, Houston, TX (US)

( * ) Notice: Subject to any disclaimer, the term of this patent is extended or adjusted under 35 U.S.C. 154(b) by 181 days.

(21) Appl. No.: 12/953,959

(22) Filed: Nov. 24, 2010

(65) Prior Publication Data

US 2012/0130119 A1 May 24, 2012

(51) Int. Cl.
| | |
|---|---|
| C07C 67/055 | (2006.01) |
| G01N 21/65 | (2006.01) |
| B01J 8/24 | (2006.01) |
| B01J 23/52 | (2006.01) |
| B01J 23/44 | (2006.01) |

(52) U.S. Cl.
CPC ...... *C07C 67/055* (2013.01); *B01J 2219/00202* (2013.01); *B01J 2219/00006* (2013.01); *B01J 23/52* (2013.01); *B01J 2219/00238* (2013.01); *B01J 2219/00231* (2013.01); *B01J 23/44* (2013.01); *B01J 2208/00274* (2013.01); *G01N 21/65* (2013.01); *B01J 8/24* (2013.01); *B01J 2219/0022* (2013.01)
USPC .......................................... 560/245; 560/243

(58) Field of Classification Search
CPC .................................................... C07C 67/055
See application file for complete search history.

(56) References Cited

U.S. PATENT DOCUMENTS

| | | | | |
|---|---|---|---|---|
| 3,300,528 | A | * | 1/1967 | Wakasa et al. ............... 560/245 |
| 3,743,607 | A | | 7/1973 | Sennewald et al. |
| 5,817,869 | A | | 10/1998 | Hinnenkamp |
| 5,932,764 | A | | 8/1999 | Morris |
| 6,022,823 | A | | 2/2000 | Augustine et al. |
| 6,255,527 | B1 | | 7/2001 | Muskett |
| 6,362,366 | B1 | | 3/2002 | Hallinan et al. |
| 6,420,595 | B1 | | 7/2002 | Choudhary et al. |
| 6,552,221 | B1 | | 4/2003 | Hallinan et al. |
| 7,476,761 | B2 | | 1/2009 | Kojima |
| 7,505,127 | B2 | | 3/2009 | Marrow et al. |
| 2012/0095259 | A1 | | 4/2012 | Salisbury et al. |

FOREIGN PATENT DOCUMENTS

WO   WO 2010/014583 A1   2/2010

OTHER PUBLICATIONS

Schrader, Fresnius' Journal of Analytical Chemistry, Raman Spectroscopy in the Near Infrared—A Most Capable Method of Vibrational Spectroscopy, 1996, 355, pp. 233-239.*

Marquardt, Center for Process Analytical Chemistry, Quantitative Raman Spectroscopy? Dispelling the Myths Through Successful Process Applications, 2007, pp. 1-63, recovered on Apr. 17 from www.strath.ac.uk/Other/cpact /presentations/2007/.../marquardt. pdf.*
PCT International Search Report & Written Opinion mailed May 16, 2012, for PCT application No. PCT/US2011/061994.
Selena E. Richards et al: "A novel approach to the quantification of industrial mixtures from the Vinyl Acetate Monomer (VAM) process using Near Infrared spectroscopic data and a Quantitative Self Modeling Curve Resolution (SMCR) methodology", Chemomimetrics and Intelligent Laboratory Systems, vol. 94, pp. 9-18, XPOO2674335, the whole document, 2008.
David D. Kragetn et al: "A Spectroscopic Study of the Homogeneous Catalytic Conversion of Ethylene to Vinyl Acetate by Palladium Acetate", Inorganic Chemistry, vol. 38, No. 2, Jan. 1, 1999, pp. 331-339, XP55025086, ISSN: 0020-1669, DOI: 10.1021/ic980399g, the whole document.
Talat Ozpozn et al: "Monitoring of the polymerization of vinylacetate by near IR FR Raman spectroscopy", Spectrochimica Acta, vol. 53, No. 1, 1997, pp. 1-7, XPOO2674945, the whole document.
"Acetic Acid" in Ullmann's Encyclopedia of Industrial Chemistry Hosea Cheung, Robin S. Tanke and G. Paul Torrence, 1999-2012, John Wiley & Sons, Inc., pp. 209-237.
J. M. Tedesco et al., :Calibration of Dispersive Raman Process Analyzers, The Society of Photo-Optical Instrumentation Engineers, vol. 3537, pp. 200-212, 1999.
S. E. Nave, "Rugged Fiber Optic Probes and Sampling Systems for Remote Chemical Analysis Via the Raman Technique," ISA, Paper No. 96-042, pp. 453-467, 1996.
M. J. Pelletier et al.: "Optical Fibers Enable Raman Instruments to Analyze Industrial Process Problems Quickly and Accurately," Raman Spectroscopy—Keeps Industry Under Control, Reprint: Photonics Spectra, 4 pages, Oct. 1997.
Sunley G. J et al: "High Productivity 1-12 Methanol Carbonylation Catalysis Using Iridium. The Cativa Process for the Manufactur of Acetic Acid", Catalysis Today, Amsterdam, NL., vol. 58, No. 4, Jan. 1, 2000, pp. 293,307, SP002264805.
Ian Lewis: "14th NIChE Conference on Micro-Reactor Technologies," Micro-Reactor Technologies: A Crticial Tool for Process Optimization and Intensification, Sep. 22, 2009, XP55012283, Retrieved from the Internet: URS: http://www.ccrhq.org/14th-niche-conference-micro-reactor-technologies.
Denis Forster: "On the Mechanism of a Rhodium-Complex-Catalyzed Carbonylation of Methanol to Acetic Acid", Journal of the American Chemical Society, vol. 98, No. 3, Feb. 1, 1976 (Feb. 12, 1986), pp. 846-848, XP55012166.
H. Chung: "Feasibility of Monitoring Acetic Acid Process Using Near-Infrared Spectroscopy", Vibrational Spectroscopy, vol. 31, No. 1, Jan. 15, 2003, pp. 125-131, XP55012187.

* cited by examiner

*Primary Examiner* — Paul A Zucker

(57) ABSTRACT

Disclosed is a method for controlling a vinyl acetate production process. The method comprises reacting ethylene, acetic acid, and an oxygen-containing gas in the presence of a catalyst in a reactor to produce vinyl acetate, measuring the concentration of a component involved in or associated with the reaction and/or any of the subsequent steps by Raman spectroscopic analysis, and adjusting the conditions in the reactor or in any of the subsequent steps in response to the measured concentration of the component to achieve a proper control of the reaction or any of the subsequent steps.

9 Claims, No Drawings

VINYL ACETATE PRODUCTION PROCESS

FIELD OF THE INVENTION

The invention relates to the preparation of vinyl acetate. More particularly, the invention relates to a method for controlling the vinyl acetate production process by Raman spectroscopy.

BACKGROUND OF THE INVENTION

Vinyl acetate is commonly produced by the reaction of ethylene, oxygen and acetic acid in the presence of a palladium-gold catalyst. See, for example, U.S. Pat. No. 3,743, 607. Palladium and gold are expensive precious metals. Therefore, many efforts have been made to increase the catalytic activity and reduce the amount of catalyst needed. For example, U.S. Pat. No. 6,022,823 teaches calcining the support impregnated with palladium and gold salts prior to reducing the metals. The catalyst shows improved activity.

The acetoxylation of ethylene to vinyl acetate is commonly performed in a gas phase, fixed bed tubular reactor. Vinyl acetate is recovered by condensation and scrubbing, and purified by distillation. Unreacted ethylene, oxygen and acetic acid are recovered by distillation and recycled to the acetoxylation. In addition to vinyl acetate, the acetoxylation produces a number of byproducts, including carbon dioxide, water, and ethylene glycol diacetate. Carbon dioxide is primarily produced by the combustion of ethylene and vinyl acetate. Carbon dioxide is removed from the reaction product mixture by distillation and absorption with a potassium carbonate solution.

U.S. Pat. No. 6,420,595 discloses a method of real time process control in a reaction system for the production of vinyl acetate from the oxidation of ethylene and acetic acid. Reaction system samples are collected from the reactor vessel feed and/or effluent and/or from columns and/or transfer lines downstream of the reactor vessel, and the concentration of one or more components in the sample is measured by an infrared analyzer. The concentration measurements are then used to make adjustments in the concentration of components in the reaction system, directly or directly or indirectly, such as by adjusting the temperature profile in a particular column, the flow rate of solution into or out of a column, or the addition or extraction of a component to or from the solution. For optimum process control, the measurements are transmitted to a control unit for real time analysis, and the adjustments are made almost instantly after the infrared analysis.

One issue associated with the use of infrared analysis in the mid infrared range of 400 to 4000 wavenumbers ($cm^{-1}$) to control a vinyl acetate production process is that the infrared signal cannot be transferred by optical fiber over long distance so that the measurement can be readily integrated into the control system. New methods for controlling the vinyl acetate production process are thus needed. Ideally, the method can directly measure the concentrations of multiple components of the vinyl acetate production process and the measured results can be directly transferred to the control room to control the production process.

SUMMARY OF THE INVENTION

The invention relates to a method for controlling a vinyl acetate production process. The method comprises (a) reacting ethylene, acetic acid, and an oxygen-containing gas in the presence of a catalyst in a reactor to produce vinyl acetate; (b) withdrawing from the reactor a gas stream comprising ethylene, acetic acid, vinyl acetate, water, and carbon dioxide; (c) separating the gas stream into an ethylene stream comprising ethylene and carbon dioxide, and a primary vinyl acetate product stream comprising vinyl acetate, water, and acetic acid; (d) separating the ethylene stream into a recovered ethylene stream and a carbon dioxide stream; (e) separating the primary vinyl acetate product stream into a vinyl acetate product stream and a recovered acetic acid stream; (f) recycling the recovered ethylene stream of step (d) and the recovered acetic acid stream of step (e) to the reactor in step (a); (g) measuring the concentration of a component involved in or associated with one or more of the above steps by Raman spectroscopic analysis; and (h) adjusting the conditions in the reactor or in any of the subsequent steps in response to the measured concentration of the component to achieve a proper control of the reaction or any of the subsequent steps.

DETAILED DESCRIPTION OF THE INVENTION

The method of the invention comprises reacting ethylene, acetic acid, and oxygen in the presence of a catalyst. The main reaction is the formation of vinyl acetate and water.

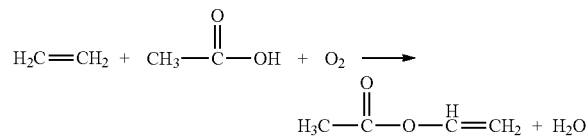

The primary side reaction is the formation of carbon dioxide by the combustion of ethylene and vinyl acetate:

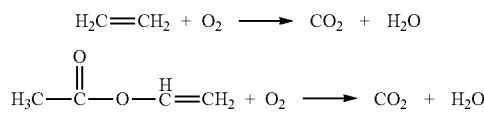

A number of other byproducts are also produced, including methyl acetate, ethyl acetate, ethylene glycol diacetate, acetaldehyde, acrolein, acetone, polyvinyl acetate, the like, and derivatives thereof.

The reaction is preferably performed in a gas phase, fixed bed tubular reactor using a supported catalyst. Preferably, the reaction is performed at a temperature within the range of 150° C. to 250° C., more preferably 175° C. to 200° C. Preferably, the reaction is performed under a pressure within the range of 50 psia to 150 psia, and more preferably within the range of 70 psia to 140 psia.

Preferably, the amount of oxygen in the combined feed is within the range of 5 mol % to 15 mol %, more preferably within the range of 5 mol % to 12 mol %. Acetic acid may be introduced into the reactor in liquid form or in vapor form. Preferably, the amount of acetic acid in the combined feed is within the range of 10 mol % to 25 mol %. Preferably, the amount of ethylene in the combined feed is within the range of 65 mol % to 80 mol %. Preferably, ethylene, oxygen and acetic acid are mixed and the mixture is then fed into the reactor as a gas.

Suitable catalysts include those known to the vinyl acetate industry. Preferably, the catalyst is a palladium-gold catalyst. Methods for preparing palladium-gold catalysts are known. For instance, U.S. Pat. No. 6,022,823, the teachings of which are incorporated herein by reference, teaches how to prepare a palladium-gold catalyst which has high activity and selectivity. Preferably, the palladium-gold catalyst is supported on an inorganic oxide. Preferably, the inorganic oxide is selected from the group consisting of alumina, silica, titania, the like, and mixtures thereof.

Preferably, the supported catalysts have palladium contents from 0.1 wt % to 3 wt % and gold contents from 0.1 wt % to 3 wt %. More preferably, the catalysts contain from 0.5 wt % to 1.5 wt % of palladium and from 0.25 wt % to 0.75 wt % of gold. The weight ratio of palladium to gold is preferably within the range of 5:1 to 1:3 and more preferably within the range of 2.5:1 to 1:1.5.

The reaction mixture is withdrawn from the reactor and separated into an ethylene stream comprising ethylene and carbon dioxide and a primary vinyl acetate product stream vinyl acetate, water, and acetic acid. Preferably, the separation of the reaction mixture is performed in an absorber tower. The reaction mixture flows to an absorber tower wherein vinyl acetate is absorbed by an acetic acid aqueous solution to form the primary vinyl acetate stream, while the ethylene stream come out of the top of the absorber tower.

The ethylene stream may contain acetic acid. Acetic acid is preferably removed in a scrubber by water washing. The overhead from the scrubber is fed to a carbon dioxide absorber to remove carbon dioxide from the ethylene stream. The carbon dioxide absorber contains a number of sieve trays where carbon dioxide reacts with potassium carbonate aqueous solution to form potassium bicarbonate. The ethylene stream is fed from the bottom of the absorber and the potassium bicarbonate is fed from the top of the absorber. The recovered ethylene stream from the carbon dioxide absorber is recycled to the reactor.

The primary vinyl acetate stream is separated into a vinyl acetate product stream and a recovered acetic acid stream. The separation is typically by distillation. The distillation is typically performed in the so-called primary tower. The recovered acetic acid stream comes as a bottoms stream of the primary tower and it usually comprises about 90 wt % of acetic acid and about 10 wt % of water. The recovered recovered acetic acid stream is optionally recycled to the abovementioned absorber tower or to a so-called acid tower wherein it is optionally mixed with the recovered ethylene stream and other feed stocks and the mixture is then fed into the reactor. The vinyl acetate stream comes as a headstream of the primary tower. It is subjected to further purifications to produce vinyl acetate product which meets the product specifications.

There are many other steps or operations associated with the vinyl acetate production process, see, for Instance, U.S. Pat. No. 6,420,595, the teachings of which are incorporated herein by reference.

The method of the invention comprises measuring the concentration of a component involved in or associated with one or more steps of the vinyl acetate production process by Raman spectroscopic analysis. Raman spectroscopy is known, for instance, see U.S. Pat. No. 7,505,127. It is an established analytical technique for chemical characterization, quantification, and identification. Raman spectroscopy provides information on molecular vibrational-rotational states. Raman shifts occur when radiation impinges on a molecule causing a change in the polarizability of the electron cloud of that molecule. In Raman, the molecule is excited from ground state to a virtual state and emits a photon as it relaxes back to a different vibrational or rotational state from where it started. Most of the incident radiation is elastically scattered (Rayleigh scatter) at the same wavelength as the source, however a small portion is inelastically scattered. This inelastic scatter is Raman scatter and includes both Stokes (emitted scatter has less energy than absorbed photon) and anti-Stokes (emitted scatter has more energy than absorbed photon) scatter. These differences in energy between the original state and this new state lead to a shift in the emitted photon's frequency away from the excitation wavelength—this is the Raman shift. Raman spectra are typically shown as plots of intensity (arbitrary units) versus Raman shift, which is often expressed in wavenumbers. In spectroscopy, wavenumbers are expressed as inverse centimeters ($cm^{-1}$).

The instrumentation used to collect and process Raman data is composed of a Raman spectrometer system, a transmittance system, a control loop, and a processor. The Raman spectrometer system contains a light source, a filter for Rayleigh scatter rejection, a monochromator, and a detector. The light source provides the excitation radiation that is transmitted through the probe to the sampling area. Scattered radiation is collected back through the probe, filtered of Rayleigh scatter, and dispersed via a monochromator. The dispersed Raman scatter is then imaged onto a detector and subsequently processed within the processor.

Typically, the light source is a visible laser, such as a frequency-doubled Nd:YAG laser (532 nm), a helium-neon laser (633 nm), or a solid-state diode laser (such as 785 nm). The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used.

The excitation radiation can be delivered to the probe, and the scattered radiation collected from the probe by any convenient means known in the art, such as conventional beam manipulation optics or fiber optic cables generally designated. For an on-line process measurement, it is particularly convenient to deliver the excitation radiation and collect the scattered radiation through fiber optic cables. It is a particular advantage of Raman spectroscopy that the excitation radiation typically used is readily manipulated fiber optically, and thus the excitation source can be positioned remotely from the sampling region.

The scattered radiation is collected and dispersed by any convenient means known in the art, such as a fiber optic probe. The collected scattered radiation is filtered to remove Rayleigh scattering and then frequency (wavelength) dispersed using a suitable dispersive element, such as a blazed grating or a holographic grating, or interferometrically (e.g., using Fourier transforms). The grating can be fixed or scanning, depending upon the type of detector used. The monochromator can be any such dispersive element, along with associated filters and beam manipulation optics.

The dispersed Raman scattering is imaged onto a detector. Typical detectors include array detectors generally used with fixed-dispersive monochromators, such as diode arrays or charge coupled devices (CCDs), or single element detectors generally used with scanning-dispersive monochromators or FT-based spectrometers, such as lead sulfide detectors and indium-gallium-arsenide detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum.

Many components associated with the vinyl acetate production process can be measured by Raman spectroscopy. Examples include water, oxygen, vinyl acetate, acetic acid, carbon dioxide, ethylene, ethanol, methyl acetate, ethyl acetate, ethylene glycol diacetate, polyvinyl acetate, acetaldehyde, acetone, acrolein, polymerization inhibitor, potassium carbonate, potassium bicarbonate, potassium acetate, potassium hydroxide, and mixtures thereof. One advantage of the invention is that the measurement can be performed online, because the scattered radiation can be readily delivered through the transmittance system to a remote location.

The method of the invention comprises adjusting the conditions in the reactor or in any of the subsequent steps in response to the measured concentration of the component to achieve a proper control of the reaction or any of the subsequent steps. The adjustments may directly or indirectly alter the concentration of one or more components in one or more locations in the vinyl acetate production process. Direct adjustment may occur by adding or extracting a component at a location in the reaction system. Indirect adjustment of component concentrations may occur in any number of ways. For example, adjusting the temperature of a solution or the temperature profile in a column affects component concentrations. Decreasing or increasing flow rates of streams from one vessel to another affects component concentrations, not just in those vessels, but may also affect concentrations in other vessels throughout the reaction system. There are many relationships between the different components comprising the solutions in the different locations of the reaction system, as understood by one skilled in the art, and the adjustment of one component concentration at one location in the reaction system can have an effect on more than one component concentration at more than one location in the reaction system.

The following example merely illustrates the invention. Those skilled in the art will recognize many variations that are within the spirit of the invention and scope of the claims.

EXAMPLE

To identify the Raman shifts and intensity of each component of each of the simulated sample types listed in Table 1, a number of experiments (normally 10) are performed for each sample type in which the concentration of said component varies while the concentrations of other components remain essentially constant or under such conditions that the other components will not interfere with the measurement of said component. These experiments are performed by preparation of multi-component standards in 20 mL sample vials at room temperature and atmospheric pressure. The concentration ranges of each component in each sample type, chosen on the basis of maximum and minimum values expected in the process, are listed in Table 1. This table also lists the Raman shifts of the components.

It should be noted that the appropriate Raman shift region used for quantitatively analyzing a particular component may vary depending on the vessel or stream in which it is being analyzed, given that a particular component may be more concentrated in one location in the process as compared to its concentration at another location and that a particular component's Raman peak will be interfered with to varying degrees depending on the sample type. This can be seen in Table 1, where, for example, water is measured around 1700 $cm^{-1}$ for the acid tower bottoms type samples and is measured in the 3200-3400 $cm^{-1}$ region for $CO_2$ absorber bottoms type samples and reactor inlet/outlet type samples.

It should also be noted that while ethylene is the olefin present in the feedstock to a vinyl acetate reactor, in order to accommodate collection of liquid phase spectra, octene is used as the olefin in these experiments. Those skilled in the art of Raman spectroscopy will recognize that the Raman shifts associated with the carbon to carbon double bond and with the C—H linkages will be similar for both olefins and that the use of octene does not detract from the claims.

For acid tower bottoms type samples, $CO_2$ absorber bottoms type samples and product tower bottoms type samples, spectroscopic data are collected using a Bruker FRA 106/S FT-Raman Spectrometer operating at 1064 nm at a power of 500 mW. For each sample, 64 spectra are collected and averaged over the range 100-3500 $cm^{-1}$. Each spectrum has an acquisition time of 60 seconds, and spectral resolution is 4 $cm^{-1}$. For reactor inlet/outlet type samples, spectroscopic data were collected using a Thermo Nicolet Almega-XR dispersive Raman spectrometer operating at 532 nm. For each sample, 32 spectra are collected and averaged over the range 100-4250 $cm^{-1}$. Each spectrum had an acquisition time of 1 second, and spectral resolution was 4 $cm^{-1}$. The results are listed in Table 1.

After collection of Raman spectra associated with the 10 multi-component standards for each sample type, eight of these spectra were used to obtain calibration models using TQ Analyst calibration software from Thermo Scientific. The component concentrations in those two calibration spectra that are not included in the calibration model are predicted by the model and compared to actual values, one of which is listed in Table 2.

TABLE 1

Components Raman Shifts

| Component | Raman Shift, cm−1 |
|---|---|
| *Product Tower Bottom* | |
| Acetic acid | 225, 875 |
| Ethyl acetate | 378, 636, 1453, 1783, 2940 |
| Vinyl acetate | 1295, 1647, 1757, 3047, 3124 |
| *Acid Tower Bottom* | |
| Acetic acid | 622, 893, 1669 |
| Ethylene glycol diacetate | 631, 1738 |
| Water | 1703 |
| *$CO_2$ Absorber Bottoms* | |
| $KHCO_3$ | 1016 |
| $K_2CO_3$ | 1065 |
| KOAc | 927 |
| Water | 3255 |
| *Reactor Inlet/Outlet* | |
| Acetic acid | 612, 884, 1419, 1663 |
| Vinyl acetate | 457, 1131, 1367, 1641, 1752, 3040, 3120 |
| Octene | 428, 1131, 1432, 1631, 2725, 2890 |
| Water | 3415 |

TABLE 2

Component concentrations: actual vs. measured

| Component | Actual, wt % | Measured, wt % |
|---|---|---|
| *Product Tower Bottoms* | | |
| Ethyl acetate | 48.5 | 49.6 |
| Vinyl acetate | 48.5 | 46.7 |
| Acetic acid | 3.0 | 2.9 |
| *Acid Tower Bottoms* | | |
| Acetic acid | 87.0 | 87.1 |
| Ethylene glycol diacetate | 10.0 | 9.7 |
| Water | 3.0 | 3.3 |
| *$CO_2$ Absorber Bottoms* | | |
| $KHCO_3$ | 10.0 | 9.5 |
| $K_2CO_3$ | 9.0 | 9.1 |
| KOAc | 4 | 4.1 |
| Water | 77.0 | 77.3 |

TABLE 2-continued

Component concentrations: actual vs. measured

| Component | Actual, wt % | Measured, wt % |
|---|---|---|
| Reactor Inlet/Outlet | | |
| Water | 2.8 | 2.0 |
| Vinyl acetate | 19.6 | 22.7 |
| Acetic acid | 26.6 | 27.3 |
| Octene | 51.0 | 51.0 |

We claim:

1. A method for the production of vinyl acetate, said method comprising:
  (a) reacting
    (i) 65 to 80 mol. % of ethylene,
    (ii) 10 to 25 mol. % of acetic acid, and
    (iii) 5 to 15 mol. % of an oxygen-containing gas in the presence of a palladium gold catalyst in a reactor to produce vinyl acetate;
  (b) withdrawing from the reactor a gas stream comprising ethylene, acetic acid, vinyl acetate, water, and carbon dioxide;
  (c) separating the gas stream into an ethylene stream comprising ethylene and carbon dioxide, and a primary vinyl acetate product stream comprising vinyl acetate, water, and acetic acid;
  (d) separating the ethylene stream into a recovered ethylene stream and a carbon dioxide stream;
  (e) separating the primary vinyl acetate product stream into a vinyl acetate product stream and a recovered acetic acid stream;
  (f) recycling the recovered ethylene stream of step (d) and the recovered acetic acid stream of step (e) to the reactor in step (a);
  (g) measuring the concentration of a component involved in or associated with one or more of the above steps by Raman spectroscopic analysis wherein the measuring step includes the step of identifying the Raman shifts and intensity of the component involved in or associated with one or more of the above steps; and
  (h) adjusting the conditions in the reactor or in any of the subsequent steps in response to the measured concentration of the component to achieve a proper control of the reaction or any of the subsequent steps.

2. The method of claim 1, wherein the separation of the gas stream in step (c) is performed in an absorber tower in which vinyl acetate is absorbed by an acetic acid aqueous solution to form the primary vinyl acetate product stream.

3. The method of claim 1, wherein the separation of the primary vinyl acetate product stream in step (e) is performed in a primary distillation tower.

4. The method of claim 1, wherein the component measured by Raman spectroscopy is selected from the group consisting of water, oxygen, vinyl acetate, acetic acid, carbon dioxide, ethylene, ethanol, methyl acetate, ethyl acetate, glycol diacetate, polyvinyl acetate, acetaldehyde, acetone, acrolein, polymerization inhibitor, potassium carbonate, potassium bicarbonate, potassium acetate, potassium hydroxide, and mixtures thereof.

5. The method of claim 1, wherein the component measured by Raman spectroscopy is selected from the group consisting of acetic acid, vinyl acetate, carbon dioxide, water, ethylene, and mixtures thereof.

6. The method of claim 5, wherein the measurement is performed in the reactor liquid phase.

7. The method of claim 5, wherein the measurement is performed in the reactor gas phase.

8. The method of claim 1, wherein the adjusting is accomplished by adding or removing a component from the reactor, from any subsequent steps, or from both.

9. The method of claim 1 wherein the adjusting is accomplished by changing a temperature profile in the reactor, in any of the subsequent steps, or in both.

* * * * *